US00PP27528P2

(12) United States Plant Patent
Probst

(10) Patent No.: US PP27,528 P2
(45) Date of Patent: Jan. 3, 2017

(54) ***COREOPSIS* PLANT NAMED 'RED CHIFFON'**

(50) Latin Name: ***Coreopsis* hybrid**
Varietal Denomination: Red Chiffon

(71) Applicant: Darrell R. Probst, Hubbardston, MA (US)

(72) Inventor: Darrell R. Probst, Hubbardston, MA (US)

( * ) Notice: Subject to any disclaimer, the term of this patent is extended or adjusted under 35 U.S.C. 154(b) by 0 days.

(21) Appl. No.: 14/756,517

(22) Filed: Sep. 14, 2015

(51) Int. Cl.
*A01H 5/02* (2006.01)

(52) U.S. Cl.
USPC ..... Plt./417

(58) Field of Classification Search
USPC ..... Plt./417
See application file for complete search history.

*Primary Examiner* — Annette Para
(74) *Attorney, Agent, or Firm* — Penny J. Aguirre

(57) ABSTRACT

A new cultivar of hybrid *Coreopsis* named 'Red Chiffon' characterized by its sturdy and well-branched plant habit reaching a 45 cm in height and 55 cm in width, its medium sized inflorescences with ray florets that are light yellow in color with a large bright red eye zone, its nearly sterile flowers that exhibit a floriferous and long bloom season that does not require deadheading with bloom commencing in early July until frost in Connecticut, its cold hardiness to at least U.S.D.A. Zone 5, and its resistance to powdery mildew and leaf spot.

2 Drawing Sheets

Botanical classification: *Coreopsis* hybrid.
Variety denomination: 'Red Chiffon'.

BACKGROUND OF THE INVENTION

The present invention relates to a new and distinct cultivar of a plant botanically of hybrid origin and known as *Coreopsis*. The new cultivar will be referred to hereafter by its cultivar name 'Red Chiffon'. 'Red Chiffon' is an herbaceous perennial grown for landscape and container use.

The new invention arose from an ongoing controlled breeding program in Hubbardston, Mass. The objective of the breeding program is to develop hybrid cultivars of *Coreopsis* with unique and superior garden attributes. In particular, to develop cultivars that are long-lived, sturdy, exhibit a true perennial habit and are cold hardy at least to U.S.D.A. Zone 5 in a wide range of flower colors and plant forms.

The Inventor made a controlled cross in August of 2011 in his test garden in Hubbardston, Mass. between an unnamed proprietary plant from the Inventor's breeding program, reference no. J 06-1, as the female parent and an unnamed proprietary plant of *Coreopsis* as the male parent. 'Red Chiffon' was selected in September 2012 as a single unique plant amongst the resulting seedlings.

Asexual propagation of the new cultivar was first accomplished by stem cuttings in Kensington, Conn. in September 2012 under the direction of the Inventor. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Red Chiffon' as unique cultivar of *Coreopsis*.

1. 'Red Chiffon' exhibits a sturdy and well-branched plant habit reaching a 45 cm in height and 55 cm in width.
2. 'Red Chiffon' exhibits medium sized inflorescences with ray florets that are light yellow in color with a large bright red eye zone.
3. 'Red Chiffon' exhibits nearly sterile inflorescences that exhibit a floriferous and long bloom season that does not require deadheading with bloom commencing in early July and lasting until frost in Connecticut.
4. 'Red Chiffon' exhibits cold hardiness to at least U.S.D.A. Zone 5.
5. 'Red Chiffon' exhibits resistance to powdery mildew and leaf spot.

The female parent of 'Red Chiffon', J 06-1, differs in having inflorescences with ray florets that are bright yellow in color, in having a taller plant height, and in having a floppy plant habit. 'Red Chiffon' can be compared to the *Coreopsis* cultivars 'Bengal Tiger' (U.S. Plant Pat. No. 25,345) and 'Route 66' (U.S. Plant Pat. No. 20,609). Both are similar to 'Red Chiffon' in having inflorescences with yellow ray florets with a red eye. 'Bengal Tiger' differs from 'Red Chiffon' in having smaller ray florets that are much deeper yellow in color, in being less cold hardy, and in being prone to powdery mildew when grown under similar conditions as 'Red Chiffon'. 'Route 66' differs from 'Red Chiffon' in having flowers that are darker yellow in color with an eye zone that is more mottled in color, in being highly fertile and in being prone to powdery mildew when grown under similar conditions as 'Red Chiffon'.

BRIEF DESCRIPTION OF THE DRAWINGS

The accompanying colored photographs illustrate the overall appearance and distinct characteristics of the new *Coreopsis*. The photographs were taken of a three month-old plant of 'Red Chiffon' as grown outdoors in a one-gallon container from a 128-cell plug in Kensington, Conn.

The photograph in FIG. 1 provides a side view of a plant of 'Red Chiffon'.

Figure 1:
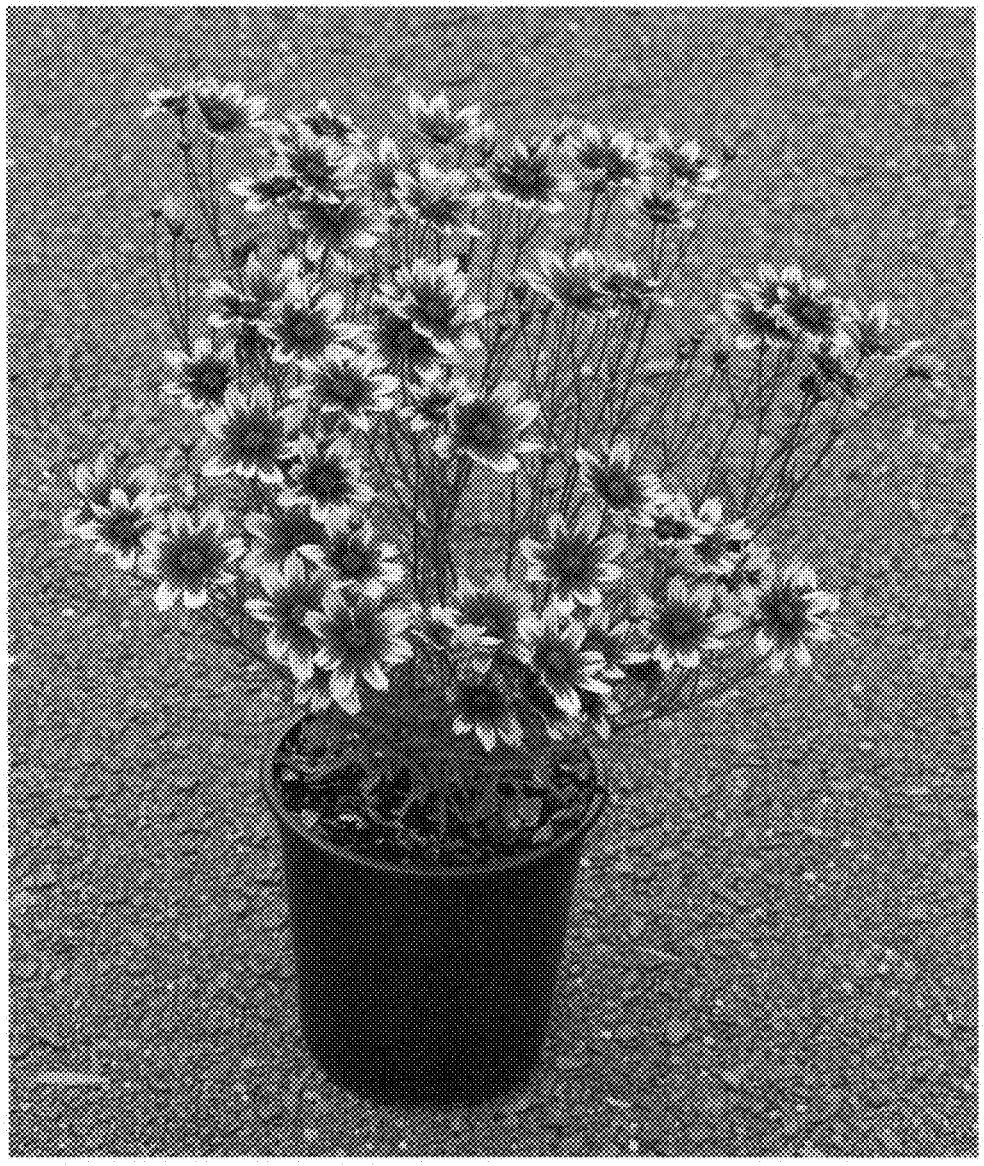
Figure 2:
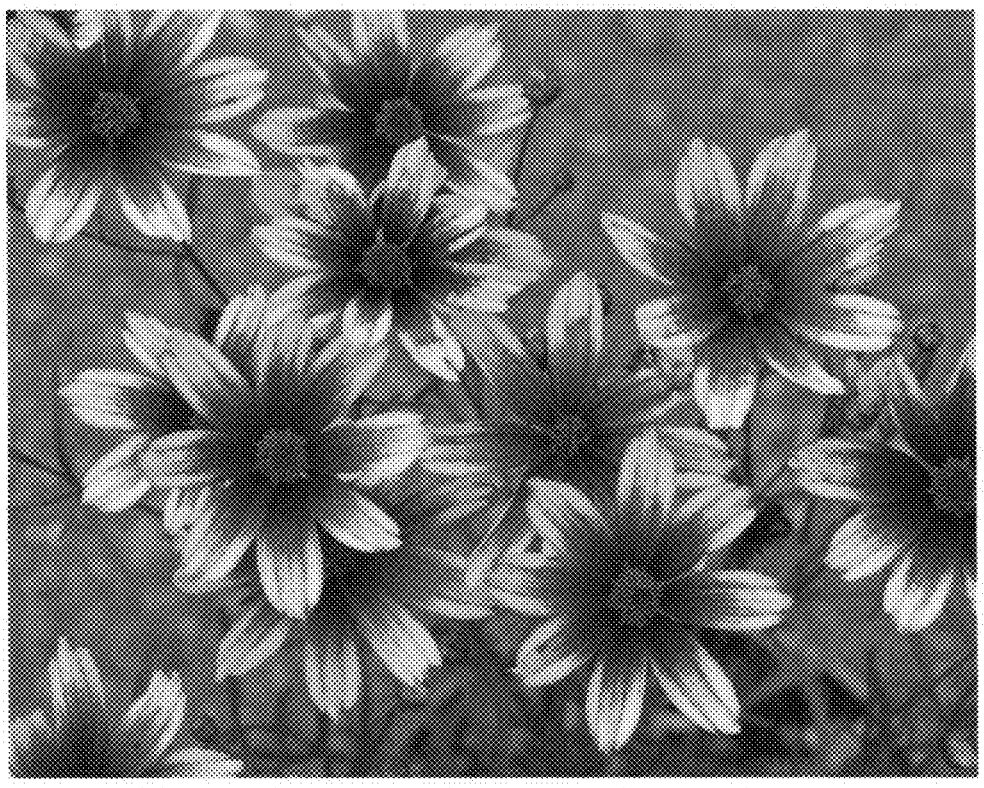

The photograph in FIG. 2 provides a close-up view of the inflorescence of 'Red Chiffon'. The colors in the photographs may differ slightly from the color values cited in the detailed botanical description, which accurately describe the colors of the new *Coreopsis*.

DETAILED BOTANICAL DESCRIPTION

The following is a detailed description of three month-old plants of 'Red Chiffon' as grown outdoors in one-gallon containers from a 128-cell plug in Kensington, Conn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Blooms from early July until frost in Kensington, Conn.

*Plant type*.—Herbaceous perennial,

*Plant habit*.—Clump-forming with sturdy well-branched stems.

*Height and spread*.—An average of 45 cm in height and 55 cm in width.

*Cold hardiness*.—At least in U.S.D.A Zone 5.

*Diseases resistance*.—Has been observed to be highly resistant to powdery mildew caused by *Podosphaera macularis* and leaf spot by *Pseudomonas cichorii*.

*Root description*.—Fibrous when young, becoming fleshy with age.

*Propagation*.—Division and terminal stem cuttings (preferred).

*Growth rate*.—Moderate to vigorous.

*Root development*.—Roots initiate in 6 to 8 days and fully develop in a 128-cell plug in about 28 days with bottom heat and rooting hormone at optimal times of the year.

Stem description:

*Shape*.—Oval, ridged.

*Stem color*.—Young; 137A and 146A, mature bark; a mix of 165A to 165B.

*Stem size*.—Main stems; an average of 28.5 cm in length and 4 mm in width, secondary; average of 13 cm in length and 2 mm in width, tertiary; 15 cm in length and 1.8 mm in width.

*Stem surface*.—Glabrous.

*Stem aspect*.—Upright to outward.

*Branching habit*.—Well-branched, an average of 9 main branches, 2 secondary branches per main stem, and 3 tertiary branches.

*Internode length*.—An average of 5.2 cm.

Foliage description:

*Leaf division*.—Simple.

*Leaf margins*.—Entire to trifid.

*Leaf size*.—Variable, up to 5 cm in length and 6 mm in width when entire, up to 5.5 cm in length and 1.1 cm in width when trifid.

*Leaf shape*.—Lanceolate when entire, lanceolate lobes when trifid.

*Leaf base*.—Clasping.

*Leaf apex*.—Acute.

*Leaf venation*.—Pinnate, inconspicuous, matches leaf color on upper and lower surface.

*Leaf attachment*.—Sessile.

*Leaf arrangement*.—Opposite.

*Leaf surface*.—Glabrous on upper and lower surface.

*Leaf color*.—Young and mature upper surface; 147A, young and mature lower surface; 147B.

Inflorescence description:

*Inflorescence type*.—Composite with a single row of ray florets surrounding disk florets in the center, forming a radiant head, inflorescences are borne on branch terminals in loose corymbs.

*Lastingness of inflorescence*.—8 to 10 days until senescence of ray flowers, longer in cool temperatures, bracts and disk flowers are persistent.

*Fragrance*.—None detected.

*Quantity of inflorescences*.—An average of 40 per main branch.

*Inflorescence size*.—Corymbs; an average of 13 cm in length and 4.5 in width, composite; an average of 1.5 cm in depth and up to 5 cm in diameter.

*Inflorescence buds*.—Average of 6 cm in depth and in diameter, spherical in shape, color; a blend of 163B, 183B, and 138A towards the base.

*Peduncle*.—Average of 5 cm in length and 1.5 mm in width, glabrous surface, a blend of 137B and 146A in color.

*Pedicle*.—Average of 8 cm in length and 0.8 mm in width, glabrous surface, a blend of 137B and 146A in color.

*Sepals*.—An average of 7, 3.5 mm in length and 1.2 mm in width, color; 137C to 137D.

Involucral bracts:

*Bract number*.—8 total, 3 outer bracts and 5 inner bracts.

*Bract arrangement*.—Outer bracts are un-fused and held outward and slightly upward, inner bracts surround receptacle in a campanulate form with apical portion un-fused, spreading, and held close to lower surface of ray florets.

*Bract size*.—Outer bracts; an average of 4.5 mm in length and 3 mm in width, inner bracts; up to 6 mm in length and 2.9 mm in width with free portion an average of 4 mm in length and 2.5 mm in width.

*Bract color*.—Inner bracts and outer bracts translucent; apex, 17C to 17D, base 143B to 143C, and margins 187A to 187B.

*Bract texture*.—Glabrous on outer and inner surfaces of outer and inner bracts.

*Bract apex*.—Acute on outer and inner bracts.

*Bract base*.—Truncate on inner and outer bracts.

*Bract margins*.—Entire.

*Bract shape*.—Outer and inner bracts; ovate.

Ray florets (sterile):

*Number*.—An average of 8 arranged primarily in one row.

*Shape*.—Obovate.

*Size*.—An average of 1.4 cm in length and 7 mm in width.

*Apex*.—2 notched.

*Base*.—Cuneate.

*Margins*.—Entire with apex notched.

*Aspect*.—Held outward to moderately upward.

*Texture*.—Glabrous on upper and lower surface.

*Color*.—When opening inner surface; 2A, base a blend of 175A and 183A, when opening outer surface; 1A to 1B, base 174A, when fully open upper surface; 6A, base 187B, when fully open lower surface; 8A, base a blend of 172A and 174A.

Disk flowers (perfect):

*Shape*.—Tubular, corolla is fused, flared at apex.

*Number*.—About 80.

*Size*.—About 4 mm in length and 0.7 mm in width.

*Color*.—En masse; 28A, corolla tube; 177A in color.

*Receptacle*.—About 4 mm in diameter and 1.5 mm in depth, a blend of 11B and 162A in color.

Reproductive organs:

*Presence*.—Disk flowers are perfect, ray flowers are sterile.

*Gynoecium*.—1 Pistil, 4 mm in length, style is very fine, translucent and 28B to 28C in color, bifid pilose stigma is 28A in color with branches about 0.8 mm in length and recurved, ovary is 1 mm in length, 0.5 mm in width, inferior, and 7B in color.

*Androcoecium*.—3 stamens, fused into tube surrounding style, 1 mm in length and 0.2 mm in width, about 200A in color, pollen is very low in quantity.

*Fruit/seed*.—No fruit or seed development was observed.

It is claimed:

1. A new and distinct cultivar of *Coreopsis* plant named 'Red Chiffon' as herein illustrated and described.

* * * * *